United States Patent [19]
Okazaki et al.

[11] Patent Number: 4,982,112
[45] Date of Patent: Jan. 1, 1991

[54] NONLINEAR OPTICAL MATERIAL

[75] Inventors: Masaki Okazaki; Tadao Shishido; Seiiti Kubodera, all of Kanagawa, Japan

[73] Assignee: Fuji Photo Film Co., Ltd., Kanagawa, Japan

[21] Appl. No.: 263,977

[22] Filed: Oct. 26, 1988

Related U.S. Application Data

[63] Continuation of Ser. No. 24,496, Mar. 11, 1987, abandoned.

[30] Foreign Application Priority Data

Mar. 11, 1986 [JP] Japan .................................. 61-53462
Mar. 12, 1986 [JP] Japan .................................. 61-53884

[51] Int. Cl.$^5$ ............................................. H03F 7/00
[52] U.S. Cl. ................................................. 307/425
[58] Field of Search ............... 548/330, 332, 333, 334, 548/325, 371, 372; 307/425

[56] References Cited

U.S. PATENT DOCUMENTS 3,988,347 10/1976 DiBella ............................. 548/371

OTHER PUBLICATIONS

*Chemical Abstracts,* 91:74623f (1979) [Yutilov, Y., et al., U.S.S.R., 664,962, 6/11/79].
*Chemical Abstracts,* 95:42998y (1981) [Bouchet, P., et al., *Tetrahedron* 1980, 36(24), 3523–33].
*Chemical Abstracts,* 56:15500f (1962) [Aliprandi, B., et al., *Ann. Chim.* (Rome), 48, 1349–56 (1958)].
Chemical Abstracts, 81:49619v (1974) [Ellis, G., et al., *J. Chem. Soc., Perkin Trans.* 1, 1974 (8), 903–9].

*Primary Examiner*—Frank Gonzalez
*Attorney, Agent, or Firm*—Sughrue, Mion, Zinn, Macpeak & Seas

[57] ABSTRACT

A nonlinear optical material comprising a compound represented by formula (I)

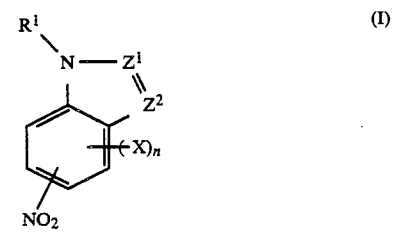

wherein $Z^1$, $Z^2$, $R^1$, X and n are as defined before, or a compound represented by formula (II)

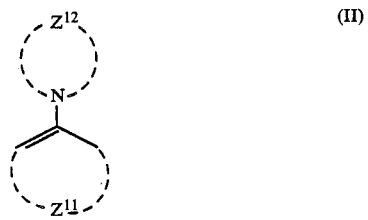

wherein $Z^{11}$ and $Z^{12}$ are as defined before. The compounds of formula (I) and (II) exhibits high transmittance to blue light and high nonlinear optical effects.

5 Claims, 1 Drawing Sheet

NONLINEAR OPTICAL MATERIAL

This is a continuation of application Ser. No. 07/024,496, filed Mar. 11, 1987, now abandoned.

FIELD OF THE INVENTION

This invention relates to a nonlinear optical material suitable for use in various elements utilizing the nonlinear optical effect such as a wavelength transformation element, etc.

BACKGROUND OF THE INVENTION

Much attention has recently been directed to materials having nonlinear optical effects, which, when irradiated with a strong laser beam, provide transmitted light having different components from incident light through the mutual interaction therebetween. Such materials are generally known as nonlinear optical materials and are described in detail, e.g., in David J. Williams (ed.), *Nonlinear Optical properties of Organic and Polymeric Materials*, ACS Symposium Series 233, American Chemical Society (1983), M. Kato & H. Nakanishi (eds.), *Organic Nonlinear Optical Materials*, CMC Co. (1985), etc.

One of the applications of nonlinear optical materials is a wavelength modulation device utilizing second harmonic generation (SHG) ascribed to the secondary nonlinear effect and sum frequency wave and difference frequency wave. Nonlinear optical materials which have been used practically in this application include inorganic perovskite structures typically exemplified by lithium niobate. In recent years, $\pi$-electron conjugated organic compounds having an electron donative group and an electron attractive group have been proved to exhibit greatly improved performance properties as nonlinear optical materials over the aforesaid inorganic materials. However, p-nitroaniline derivatives known to exhibit high SHG performance, such as 2-methyl-4-nitroaniline (MNA), 2-N,N-dimethylamino-5-nitroacetoanilide (DAN), etc., show low transmittances to blue light due to their strong yellow color. Substitution of a carbon atom of the benzene nucleus of nitroanilines by a nitrogen atom, etc., has been studied, but fully satisfactory results are not necessarily obtained. Therefore, it has been desired to develop a nonlinear optical material having a high transmittance of blue light.

SUMMARY OF THE INVENTION

One object of this invention is to provide a novel organic compound having a high transmittance of blue light and exhibiting high nonlinear optical effects.

It has now been found that the object of this invention can be accomplished by using certain compounds having a nitro group-substituted aromatic and heterocyclic ring structure.

The present invention is directed to a nonlinear optical material comprising a compound represented by formula (I) or (II) shown below or an acid adduct thereof.

Formula (I) is represented by

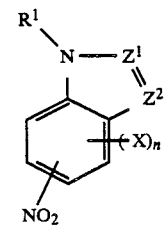

wherein $Z^1$ and $Z^2$ (which may be the same or different) each represents a nitrogen atom or $CR^2$, wherein $R^2$ represents a hydrogen atom, a substituted or unsubstituted alkyl group, or a substituted or unsubstituted aryl group, and at least one of $Z^1$ and $Z^2$ being a nitrogen atom; X represents a substituted or unsubstituted alkyl group, a substituted or unsubstituted aryl group, a halogen atom, a substituted or unsubstituted alkoxy group, a substituted or unsubstituted aryloxy group, a substituted or unsubstituted acylamino group, a substituted or unsubstituted carbamoyl group, a substituted or unsubstituted sulfamoyl group, a substituted or unsubstituted acyloxy group, a substituted or unsubstituted alkyloxycarbonyl group, a substituted or unsubstituted aryloxycarbonyl group, a substituted or unsubstituted alkyloxysulfonyl group, a substituted or unsubstituted alkylthio group, a substituted or unsubstituted arylthio group, a hydroxyl group, a thiol group, a carboxyl group, a substituted or unsubstituted ureido group, a cyano group, a substituted or unsubstituted alkylsulfonyl group, a substituted or unsubstituted arylsulfonyl group, a substituted or unsubstituted alkylsulfinyl group, a substituted or unsubstituted arylsulfinyl group, or a nitro group; n represents 0 or an integer of from 1 to 3; and $R^1$ represents a hydrogen atom, a substituted or unsubstituted alkyl group, a substituted or unsubstituted aryl group, or a substituted or unsubstituted acyl group.

Formula (II) is represented by

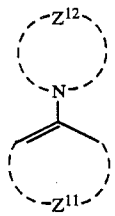

wherein $Z^{11}$ represents an atomic group forming a substituted or unsubstituted 5- to 6-membered aromatic ring having at least one nitro group as a substituent; and $Z^{12}$ represents an atomic group forming a substituted or unsubstituted pyrrole, imidazole, pyrazole, triazole or tetrazole ring.

BRIEF DESCRIPTION OF ACCOMPANYING DRAWINGS

FIGS. 1 and 2 each show spectral transmittances of compounds according to the present invention and comparative compounds in ethanolic solution. In these figures, the abscissa indicates wavelengths (nm) and the ordinate indicates transmittances (T%).

DETAILED DESCRIPTION OF THE INVENTION

Figure 1:
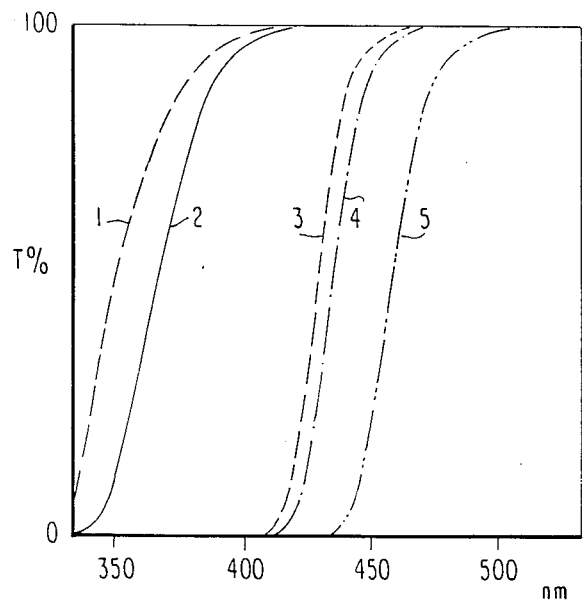

As is apparent from Examples hereinafter described, the nonlinear optical material of the present invention represented by formulae (I) and (II) are particularly useful as a material for wavelength converter elements. However, the utility of the nonlinear optical materials of the present invention is not limited to such wavelength converter elements, and the materials can be used for other various elements utilizing the nonlinear optical effect. Examples of such elements include optical bistable elements, for example, an optical memory element, an optical pulse wave controlling element, an optical limiter, a differential amplifier, a phototransistor, an A/D converter, an optical logic element, an optical multi-vibrator, an optical flip-flop circuit, etc., as well as an optical modulator, a phase conjugating optical element, etc.

The terminology "acid adduct" as used herein means an adduct of the compound represented by formula (I) or (II) with, usually, one molecule of an organic acid, e.g., a carboxylic acid, a sulfonic acid, etc., or an inorganic acid, e.g., sulfuric acid, hydrochloric acid, nitric acid, phosphoric acid, etc.

In formula (I), the alkyl group as represented by Z, $R^1$, or $R^2$ includes a methyl group, an ethyl group, an isopropyl group, a butyl group, a t-butyl group, an octyl group, a t-octyl group, a decyl group, a hexadecyl group, a docosyl group, a 2-hydroxyethyl group, a carboxymethyl group, a cyanomethyl group, a 2-methoxyethyl group, a benzyl group, a 2 phenylethyl group, a trifluoromethyl group, a 3-(2-benzoimidazoly1)propyl group, etc. The aryl group as represented by X, $R^1$, or $R^2$ includes a phenyl group, a 4-methylphenyl group, a 3-methoxyphenyl group, a 4-chlorophenyl group, etc. The halogen atom as represented by X includes a fluorine atom, a chlorine atom, a bromine atom, and an iodine atom. The alkoxy group includes a methoxy group, a butoxy group, a 2-methoxyethoxy group, a benzyloxy group, a 2-phenylethoxy group, etc. The aryloxy group includes a phenoxy group, a 4-t-butylphenoxy group, a 4-chlorophenoxy group, etc. The acylamino group includes an acetylamino group, a methanesulfonylamino group, a benzoylamino group, a 4-methylbenzenesulfonylamino group, etc. The carbamoyl group includes a carbamoyl group, an N-methylcarbamoyl group, an N-ethylcarbamoyl group, an N-phenylcarbamoyl group, etc. The sulfamoyl group includes a sulfamoyl group, an N-methylsulfamoyl group, an N-phenylsulfamoyl group, etc. The acyloxy group includes an acetyloxy group, a pivaloyloxy group, a benzoyloxy group, a benzenesulfonyloxy group, etc. The ureido group includes a methylureido group, an ethylureido group, a phenylureido group, etc.

Among the compounds represented by formula (I), preferred are those represented by formula (III) shown below and acid adducts thereof.

Formula (III) is represented by

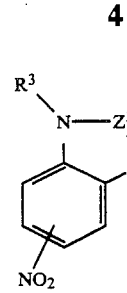

wherein $Z^3$ and $Z^4$ each has the same meaning as $Z^1$ and $Z^2$; and $Z^3$ has the same meaning as $R^1$.

More preferred of the compounds represented by formula (III) are those represented by formula (IV) or (V) shown below and acid adducts thereof.

Formula (IV) is represented by

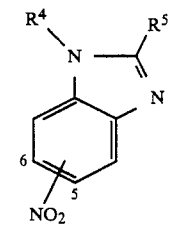

wherein $R^4$ has the same meaning as $R^1$; $R^5$ has the same meaning as $R^2$; and the nitro group ($NO_2$) is bonded at the 5- or 6-position.

Formula (V) is represented by

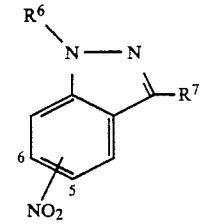

wherein $R^6$ has the same meaning as $R^1$; $R^7$ has the same meaning as $R^2$; and the nitro group ($NO_2$) is bonded at the 5- or 6-position.

In formula (II), the 5- to 6-membered aromatic ring formed by $Z^{11}$ includes a thiazole ring, an oxazole ring, an imidazole ring, a pyridine ring, a pyrimidine ring, and a benzene ring. These rings may be condensed rings.

Substituents for these aromatic rings include a substituted or unsubstituted alkyl group, a substituted or unsubstituted aryl group, a halogen atom, a substituted or unsubstituted alkoxy group, a substituted or unsubstituted aryloxy group, a substituted or unsubstituted acylamino group, a substituted or unsubstituted carbamoyl group, a substituted or unsubstituted sulfamoyl group, a substituted or unsubstituted acyloxy group, a substituted or unsubstituted alkyloxycarbonyl group, a substituted or unsubstituted aryloxycarbonyl group, a substituted or unsubstituted alkyloxysulfonyl group, a substituted or unsubstituted aryloxysulfonyl group, a substituted or unsubstituted alkylthio group, a substituted or unsubstituted arylthio group, a hydroxyl group, a thiol group, a carboxyl group, a substituted or unsubstituted ureido group, a cyano group, a substituted or unsubstituted alkylsulfonyl group, a substituted or unsubstituted arylsulfonyl group, a substituted or unsubstituted alkylsulfinyl group, a substituted or unsubstituted arylsulfinyl group, a nitro group, etc.

Specific examples of the alkyl group, aryl group, halogen atom, alkoxy group, aryloxy group, acylamino group, carbamoyl group, sulfamoyl group, acyloxy group, and ureido group are the same as enumerated with respect to formula (I).

The pyrrole ring formed by $Z^{12}$ includes pyrrole, indole, 2-methylindole, 5-methoxyindole, 5-hydroxyindole, L-tryptophanecarbazole, 3-carboxyindole, 2,5-dimethylpyrrole, etc. The imidazole ring includes imidazole, 2-methylimidazole, 2-ethylimidazole, 2-undecylimidazole, 2-phenylimidazole, 2,4-dimethylimidazole, 2-ethyl-4-methylimidazole, L-histidine, 4,5-diphenylimidazole, 2,4,5-triphenylimidazole, benzimidazole, 2-methylbenzimidazole, 2-methyl-5-chlorobenzimidazole, 2-methyl-5,6-dichlorobenzimidazole, 2-methyl-5-chloro-6-cyanobenzimidazole, 2-mercasptobenzimidazole, etc. The pyrazole ring includes pyrazole, 3,5-dimethylpyrazole, 3,5-diphenylpyrazole, 4-bromo-3,5-dimethylpyrazole, 3-methylpyrazole, indazole, etc. The triazole ring includes 1,3,4-triazole, 1,2,4-triazole, 2-chloro-1,3,4-triazole, 2,5-dimethyl-1,3,4-triazole, 3,5-diphenyl-1,2,4-triazole, benzotriazole, etc. The tetrazole ring includes tetrazole, 5-phenyltetrazole, etc.

The ring as represented by $Z^{12}$ may have a substituent which forms a dimer of the compound of formula (II), e.g., —S—.

Specific but non-limitative examples of the compounds represented by formula (I) (Compound Nos. 1 to 23) and the compounds represented by formula (II) (Compound Nos. 24 to 52) are shown below.

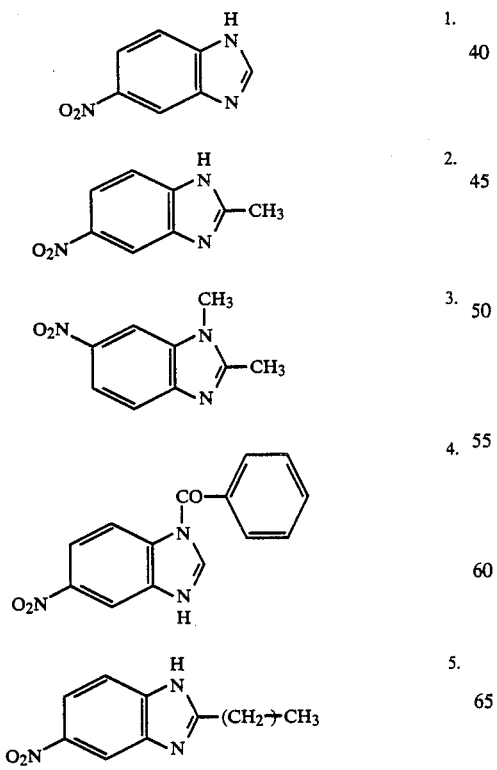

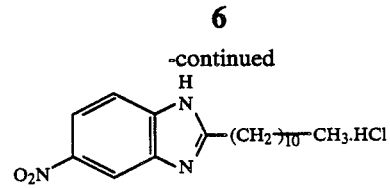

6.

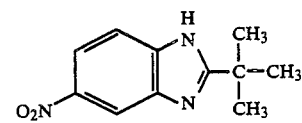

7.

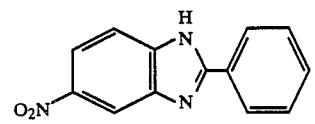

8.

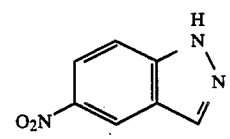

9.

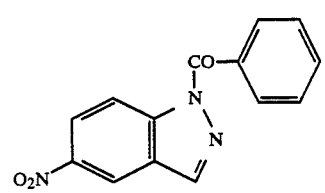

10.

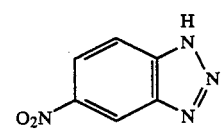

11.

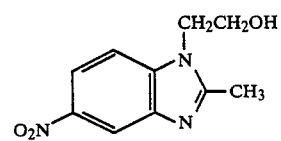

12.

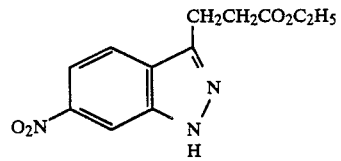

13.

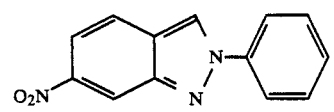

14.

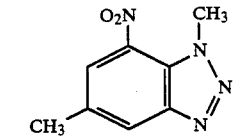

15.

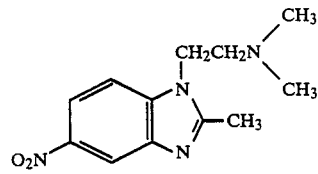

16.

-continued
17. 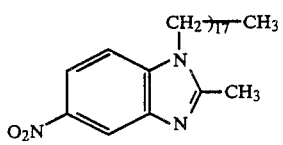
18. 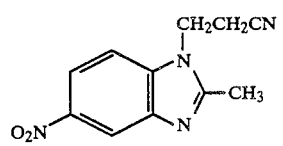
19. 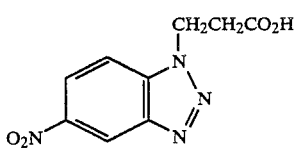
20. 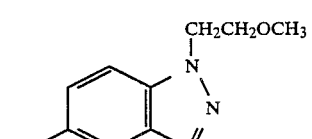
21. 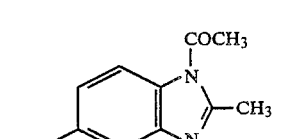
22. 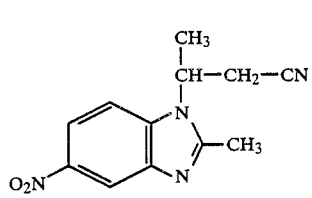
23. 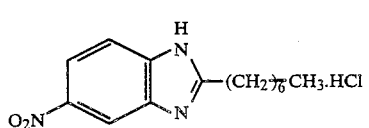
24. 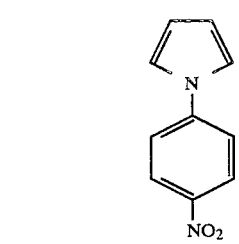
25. 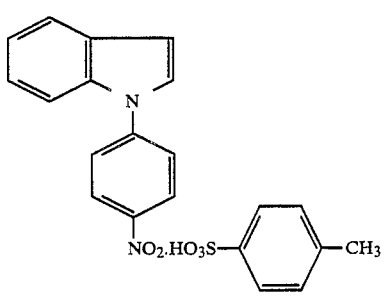
-continued
26. 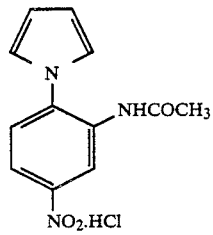
27. 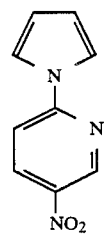
28. 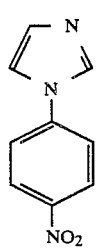
29. 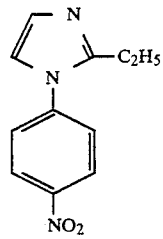
30. 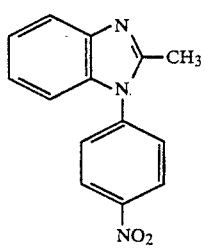
31. 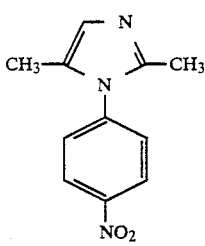

-continued
32. 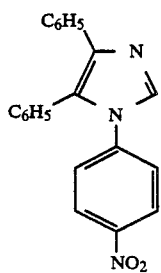
33. 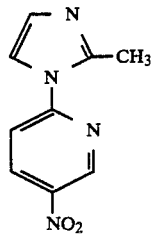
34. 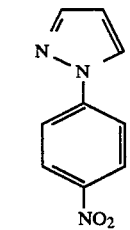
35. 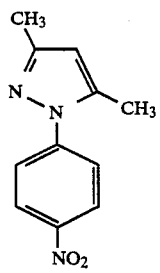
36. 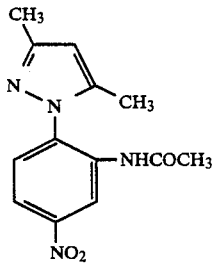
37. 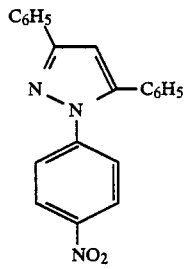
-continued
38. 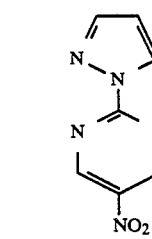
39. 
40. 
41. 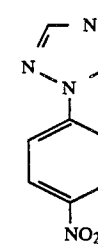
42. 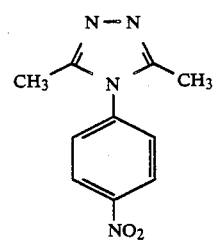
43. 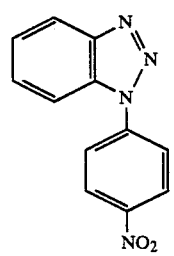

-continued

44. 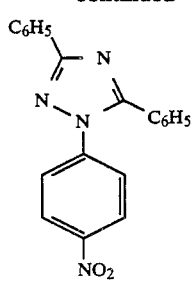

45. 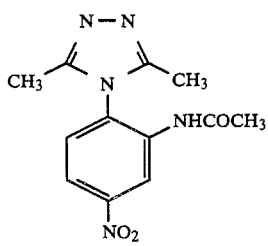

46. 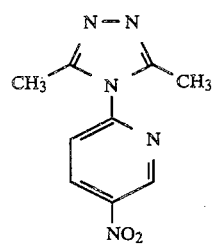

47. 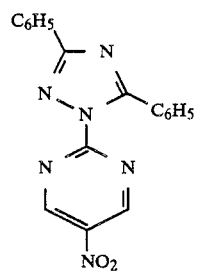

48. 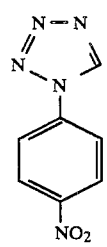

49. 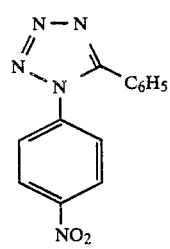

-continued

50. 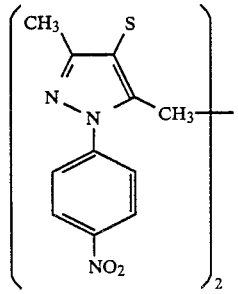

51. 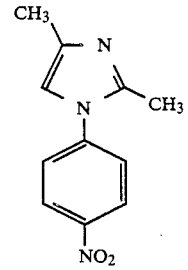

52. 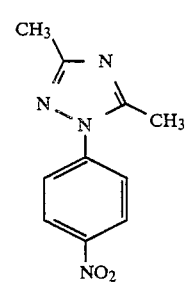

Most of the compounds of formula (I) are known per se and can be synthesized, for example, by the process described in R.C. Elderfield, *Heterocyclic Compounds*, Vols. 5 and 7, John Wiley & Sons, Inc., New York, London. They are also available as commercial products sold by Wako Pure Chemicals, Tokyo Chemical Industry Co., Ltd., Aldrich, etc.

Synthesis examples for typical compounds of formula (I) are shown below.

SYNTHESIS EXAMPLE 1

Synthesis of Compound No. 2

To 80 ml of acetic anhydride was added 15 g of 3-nitro-1,2-diaminobenzene, and 1 ml of concentrated hydrochloric acid was carefully added thereto dropwise. The mixture was heat-refluxed while stirring for 3 hours. The reaction mixture was cooled to room temperature, and the precipitated crystals were collected by filtration under reduced pressure and added to a 10 wt% sodium hydroxide aqueous solution, followed by stirring at 70° C. for 1 hour. The resulting solution was neutralized with concentrated hydrochloric acid while ice-cooling. The thus formed crystals were collected by filtration under reduced pressure and recrystallized from methanol to give 6.5 g of Compound No. 2 having a melting point of 223° C. as colorless tabular crystals.

SYNTHESIS EXAMPLE 2

Synthesis of Compound No. 5

Thirty grams of valeric acid and 22 g of o-phenylenediamine were mixed and heated at reflux for 2 hours. The reaction mixture was poured into ethanol and then neutralized with a potassium hydroxide aqueous solution. The resulting crystals were filtered and recrystallized from a mixed solvent of ethanol and water to obtain 14 g of needle-like crystals. Ten grams of the resulting crystals were added to 60 ml of sulfuric acid, and 6.5 ml of nitric acid was slowly added thereto dropwise under ice-cooling and stirring. After the dropwise addition, the reaction mixture was stirred for 2 hours under ice-cooling, poured into ice-water, and then neutralized with aqueous ammonia. The thus precipitated crystals were recrystallized from a mixed solvent of ethanol and water to yield 4.5 g of Compound No. 5 having a melting point of 139° C. as white crystals.

The compounds of formula (II) can be easily synthesized according to the following reaction scheme:

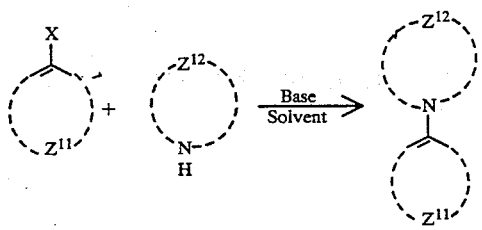

wherein $Z^{11}$ and $Z^{12}$ are as defined above; and X represents a halogen atom.

The base which can be used in the above reaction includes organic bases, e.g., pyridine, triethylamine, 1,8-diazabicyclo[5,4,0]-7-undecene, etc., and inorganic bases, e.g., potassium carbonate, sodium hydrogencarbonate, potassium t-butoxide, sodium hydride, sodium hydroxide, etc. The solvent to be used includes hydrocarbons, e.g., n-hexane, etc.; ethers, e.g., tetrahydrofuran, 1,2-dimethoxyethane, etc., amides, e.g., N,N-dimethylformamide, N-methylpyrrolidone, etc.; sulfur-containing compounds, e.g., dimethyl sulfoxide, sulforan, etc.; nitriles, e.g., acetonitrile, etc.; esters, e.g., ethyl acetate, etc.; and the like. Of these, amides, sulfur-containing compounds, and nitriles are preferred.

The reaction temperature preferably ranges from −10° C. to 150° C., and more preferably from 20° C. to 100° C.

Synthesis examples for the typical compounds of formula (II) are shown below.

SYNTHESIS EXAMPLE 3

Synthesis of Compound No. 24

Five milliliters of N,N-dimethylformamide were added to a mixture consisting of 1.41 g (10 mmol) of 4-fluoronitrobenzene, 0.67 g (10 mmol) of pyrrole, and 1.38 g (10 mmol) of potassium carbonate, and the resulting mixture was heated at 90° C. for 4 hours while stirring. The reaction mixture was poured into water, and the thus precipitated crystals were collected by filtration and washed with water. The crude crystals were recrystallized twice from isopropanol to obtain 1.21 g (64.4%) of Compound No. 24 having a melting point of 188° to 189° C.

$\lambda_{max}^{C_2H_5OH} = 326$ nm

Elementary Analysis:
Found (%): C 64.05, H 4.17, N 14.89
Calcd (%): C 63.82, H 4.28, N 14.89

SYNTHESIS EXAMPLE 4

Synthesis of Compound No. 29

The same procedure as described in Synthesis Example 3 was repeated, except that the pyrrole as used in Synthesis Example 3 was replaced with 2-ethylimidazole to obtain 1.63 g (75.1%) of Compound No. 29 having a melting point of 161° to 162° C.

$\lambda_{max}^{C_2H_5OH} = 269$ nm

Elementary Analysis:
Found (%): C 60.94, H 4.96, N 19.40
Calcd (%): C 60.82, H 5.10, N 19.34

SYNTHESIS EXAMPLE 5

Synthesis of Compound No. 35

The same procedure as described in Synthesis Example 3 was repeated, except for replacing the pyrrole with 3,5-dimethylpyrazole to obtain 1.51 g (69.6%) of Compound No. 35 having a melting point of 102° C.

$\lambda_{max}^{C_5H_5OH} = 312$ nm

Elementary Analysis:
Found (%): C 60.76, H 4.91, N 19.26
Calcd (%): C 60.82, H 5.10, N 19.34

SYNTHESIS EXAMPLE 6

Synthesis of Compound No. 52

The same procedure as described in Synthesis Example 3 was repeated, except for replacing the pyrrole with 1H-3,5-dimethyl-1,2,4-triazole to obtain 1.65 g (75.6%) of Compound No. 52 having a melting point of 156° to 156.5° C.

$\lambda_{max}^{C_2H_5OH} = 285$ nm

Elementary Analysis:
Found (%): C 55.27, H 4.65, N 25.58
Calcd (%): C 55.04, H 4.62, N 25.68

The compounds of formula (I) or (II) according to the present invention can be used as nonlinear optical materials in various forms, such as powders, molecular inclusions in a host lattice (e.g., polymers, clathreate compounds, solid solutions, liquid crystals, etc.), thin layers deposited on a support (e.g., Langmuir-Brodiet membrane), single crystals, solutions, and the like.

The compounds of formula (I) or (II) may also be used as linked to polymers, polydiacetylenes, etc. in the form of a pendant group.

The details of these forms of compounds and processes for obtaining these forms are described in the above-recited references to D. J. Williams (ed.), etc.

The present invention is now illustrated in greater detail with reference to the following examples, but it should be understood that these examples are not deemed to limit the present invention.

EXAMPLE 1

The compounds of the invention shown in Table 1 were evaluated for second harmonic generation performance in accordance with the method described in S. K. Kurtz & T. T. Perry, Journal of Applied Physics, Vol. 39, p 3798 (1968).

Each of the compounds in the form of powder was packed in a glass cell, and irradiated with an Nd:YAG laser beam having a wavelength of 1064 nm (20 mW pulse) to observe generation of green light. The results obtained are shown in Table 1.

TABLE 1

| Compound No. | Generation of Green Light |
|---|---|
| 1 | observed |
| 6 | observed |
| 7 | observed |
| 8 | observed |
| 23 | observed |

EXAMPLE 2

The same procedure as described in Example 1 was repeated except for using test compounds shown in Table 2. The generated green light was passed through a filter and a monochromator to isolate a wave length of 532 nm, and the monochormatic light was detected with a photomultiplier to determine a relative SHG strength, taking that of urea as a standard (1). The results obtained are shown in Table 2.

TABLE 2

| Test Compound | Relative SHG Strength | Remark |
|---|---|---|
| urea | 1 standard | Comparison |
| Compound No. 2 | 12 | Invention |
| Compound No. 10 | 5 | Invention |

EXAMPLE 3

The same procedure of Example 2 was repeated except for using a dye laser (dye: DTTC produced by Eastman Kodak; solvent: dimethyl sulfoxide) having a wavelength of 870 nm which was excited with the second harmonics of an Nd:YAG laser beam as a ray source. The intensity of blue light having a wavelength of 435 nm was measured in the same manner as in Example 2. The results obtained are shown in Table 3.

TABLE 3

| Compound Used | SHG Strength | Remark |
|---|---|---|
| urea | 1 standard | Comparison |
| MNA* | 2 | " |
| Compound No. 2 | 13 | Invention |
| Compound No. 10 | 8 | " |
| Compound No. 1 | 1 | " |

Note:

*MNA: 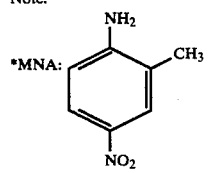

As is apparent from Examples 1 to 3, the compounds according to the present invention are useful as excellent nonlinear optical materials.

EXAMPLE 4

In order to evaluate transmittance to blue light, an ethanolic solution containing $4 \times 10^{-4}$ mol/l of each of the following compounds was measured for transmittance to wavelengths shown in FIG. 1. The results obtained are shown in FIG. 1.

| Test Compound | Line No. in FIG. 1 | Remark |
|---|---|---|
| Compound No. 10 | (1) | Invention |
| Compound No. 2 | (2) | " |
| PNP** | (3) | Comparison |
| MNA | (4) | " |
| PAN*** | (5) | " |

Note:

PNP** 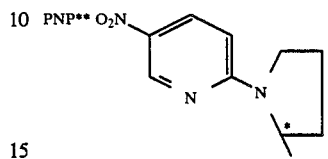

*an optically active asymmetric carbon atom

PAN*** 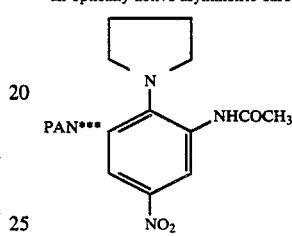

As can be seen from FIG. 1, the compounds in accordance with the present invention are excellent in transmittance to blue light.

EXAMPLE 5

The same procedure as in Example 2 was repeated except for using the compounds shown in Table 4 below to evaluate SHG strength. The results obtained are shown in Table 4.

TABLE 4

| Compound Used | SHG Strength |
|---|---|
| urea | 1 (standard) |
| Compound No. 24 | 9.6 |
| Compound No. 29 | 6.4 |
| Compound No. 35 | 16.0 |
| Compound No. 52 | 12.8 |
| Compound No. 50 | 3.6 |

EXAMPLE 6

In order to evaluate transmittance to blue light, an ethanolic solution containing $4 \times 10^{-4}$ mol/liter of each of the following compounds was determined. The results obtained are shown in FIG. 2.

TABLE 5

Figure 2:
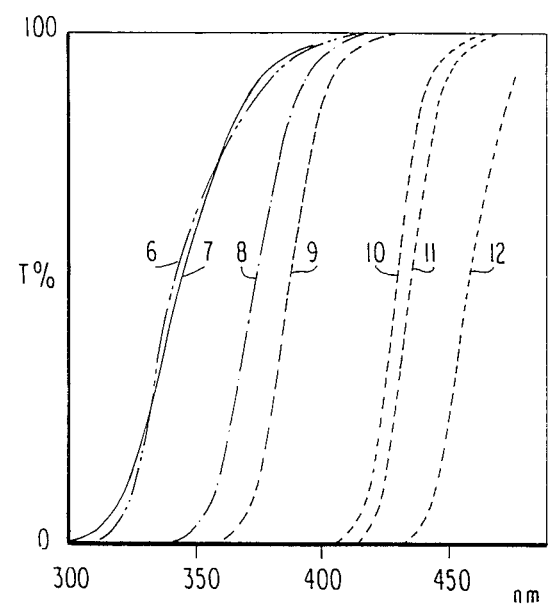

| Test Compound | Line No. in FIG. 2 | Remark |
|---|---|---|
| Compound No. 52 | (6) | Invention |
| Compound No. 29 | (7) | Invention |
| Compound No. 35 | (8) | Invention |
| Compound No. 24 | (9) | Invention |
| PNA | (10) | Comparison |
| MNA | (11) | Comparison |
| PAN | (12) | Comparison |

As is apparent from FIG. 2, the compounds according to the present invention are excellent in transmittance of blue light.

As demonstrated by the results of Examples 5 and 6, the compounds of the present invention exhibit high non-linear optical properties and high transmittance of blue light.

While the invention has been described in detail and with reference to specific embodiments thereof, it will be apparent to one skilled in the art that various changes and modifications can be made therein without departing from the spirit and scope thereof.

What is claimed is:

1. A method for converting a wavelength of a laser beam comprising irradiating with a laser beam, a nonlinear optical material comprising a compound represented by formula (I) or an acid salt thereof

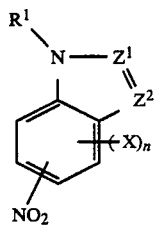

wherein $Z^1$ and $Z^2$ each represent a nitrogen atom or $CR^2$, wherein $R^2$ represents a hydrogen atom, a substituted or unsubstituted alkyl group having up to 11 carbon atoms, or a substituted or unsubstituted aryl group, and at least one of $Z^1$ and $Z^2$ is a nitrogen atom; and X represents a substituted or unsubstituted alkyl group, a substituted or unsubstituted aryl group, a halogen atom, a substituted or unsubstituted alkoxy group, a substituted or unsubstituted aryloxy group, a substituted or unsubstituted acylamino group, a substituted or unsubstituted carbamoyl group, a substituted or unsubstituted sulfamoyl group, a substituted or unsubstituted acyloxy group, a substituted or unsubstituted alkkyloxycarbonyl group, a substituted or unsubstituted aryloxycarbonyl group, a substituted or unsubstituted alkyloxysulfonyl group, a substituted or unsubstituted aryloxysulfonyl group, a substituted or unsubstituted alkylthio group, a substituted or unsubstituted atylthio group, a hydroxyl group, a thiol group, a carboxyl group, a substituted or unsubstituted ureido group, a cyano group, a substituted or unsubstituted alkylsulfonyl group, a substituted or unsubstituted arylsulfonyl group, a substituted or unsubstituted alkylsulfinyl group, a substituted or unsubstituted arylsulfinyl group, or a nitro group; n represents 0 or an integer of from 1 to 3; and $R^1$ represents a hydrogen atom, a substituted or unsubstituted alkyl group, a substituted or unsubstituted aryl group, or a substituted or unsubstituted acyl group.

2. The method of claim 1, wherein said compound represented by formula (I) is represented by formula (III)

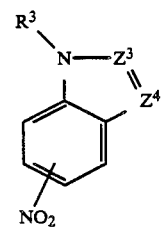

wherein $Z^3$ and $Z^4$ each has the same meaning as $Z^1$ and $Z^2$; and $R^3$ has the same meaning as $R^1$.

3. The method of claim 2, wherein said compound represented by formula (III) is represented by formula (IV)

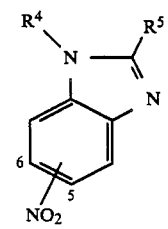

wherein $R^4$ has the same meaning as $R^1$; $R^5$ has the same meaning as $R^2$; and the nitro group ($NO_2$) is bonded at the 5- or 6-position.

4. The method of claim 2, wherein said compound represented by formula (III) is represented by formula (V)

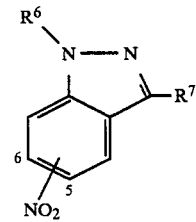

wherein $R^6$ has the same meaning as $R^1$; $R^7$ has the same meaning as $R^2$; and the nitro group ($NO_2$) is bonded at the 5- or 6-position.

5. The method of claim 1 wherein said material is used as a wavelength converter element.

* * * * *